(12) United States Patent
Rosch et al.

(10) Patent No.: US 6,497,694 B1
(45) Date of Patent: Dec. 24, 2002

(54) DISPOSABLE WASTE CONTAINMENT GARMENT

(75) Inventors: Paulette Mary Rosch, Sherwood; Ingrid Christine Hollrah, Neenah; Roxanne Belinda Hallock, Oshkosh, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 08/283,101

(22) Filed: Jul. 29, 1994

(51) Int. Cl.[7] .................................................. A61F 13/15
(52) U.S. Cl. .................................................. 604/385.28
(58) Field of Search .............................. 604/373, 385.1, 604/385.2, 393–402, 385.01, 385.03, 385.04, 385.05, 387, 385.101, 385.28, 385.24

(56) References Cited

U.S. PATENT DOCUMENTS

| | | | |
|---|---|---|---|
| 876,173 A | 1/1908 | Guttman | |
| 2,629,380 A | 2/1953 | Schweikert | 128/284 |
| 2,678,648 A | 5/1954 | De Woskin | 128/288 |
| 2,842,129 A | 7/1958 | Ernstorff | 128/288 |
| 3,025,856 A | 3/1962 | Burwell et al. | 128/288 |
| 3,043,307 A | 7/1962 | Weston | 128/295 |
| 3,237,625 A | 3/1966 | Johnson | 128/288 |
| 3,368,563 A | 2/1968 | Scheier | 128/288 |
| 3,520,303 A | 7/1970 | Endres | 128/287 |
| 3,599,640 A | 8/1971 | Larson | 128/286 |
| 3,613,687 A | 10/1971 | Kennedy | 128/288 |
| 3,636,953 A | 1/1972 | Benevento | 128/291 |
| 3,648,699 A | 3/1972 | Anderson et al. | 128/288 |
| 3,714,946 A | 2/1973 | Rudes | 128/295 |
| 3,720,212 A | 3/1973 | Kaupin | 128/288 |
| 3,860,003 A | 1/1975 | Buell | 128/287 |
| 3,938,522 A | 2/1976 | Repke | 128/287 |
| 4,114,621 A | 9/1978 | Mims, Jr. | 128/288 |
| 4,145,763 A | 3/1979 | Abrams et al. | 2/403 |
| 4,227,531 A | 10/1980 | McLeod | 128/288 |
| 4,324,245 A | 4/1982 | Mesek et al. | 128/287 |
| 4,337,771 A | 7/1982 | Pieniak et al. | 128/287 |
| 4,340,563 A | 7/1982 | Appel et al. | 264/518 |
| 4,388,075 A | 6/1983 | Mesek et al. | 604/385 |
| 4,405,297 A | 9/1983 | Appel et al. | 425/72 S |
| 4,555,245 A | 11/1985 | Armbruster | 604/396 |
| 4,573,988 A | 3/1986 | Pieniak et al. | 604/379 |
| 4,606,964 A | 8/1986 | Wideman | 428/152 |
| 4,639,949 A | 2/1987 | Ales et al. | 2/402 |
| 4,657,539 A * | 4/1987 | Hasse | 604/385.2 |
| 4,657,802 A | 4/1987 | Morman | 428/152 |
| 4,699,620 A | 10/1987 | Bernadin | 604/385 A |
| 4,704,116 A * | 11/1987 | Enloe | 604/385.2 |
| 4,720,415 A | 1/1988 | Vander Wielen et al. | 428/152 |
| 4,738,676 A | 4/1988 | Osborn, III | 604/385 R |
| 4,738,677 A * | 4/1988 | Foreman | 604/385.2 |
| 4,747,846 A | 5/1988 | Boland et al. | 604/38 A |
| 4,795,454 A * | 1/1989 | Dragoo | 604/385.2 |
| 4,798,603 A | 1/1989 | Meyer et al. | 604/378 |

(List continued on next page.)

FOREIGN PATENT DOCUMENTS

| | | | |
|---|---|---|---|
| CA | 1299321 | 3/1988 | |
| EP | 0 532 005 | 3/1993 | A61F/13/15 |
| EP | 0539703 A1 | 5/1993 | A61F/13/15 |
| GB | 2 140 471 A | 11/1984 | |
| GB | 2269978 | 3/1994 | |
| GB | 2269998 | 3/1994 | |
| GB | 2269999 | 3/1994 | |
| WO | 94/02093 | 2/1994 | A61F/13/15 |
| WO | 95/18589 | 7/1995 | A61F/13/15 |

Primary Examiner—Dennis Ruhl
(74) Attorney, Agent, or Firm—Brinks Hofer Gilson & Lione (57) ABSTRACT

A disposable waste containment article includes a waste containment structure that has an absorbent composite which is positioned between the wearer and cover and a pair of containment flaps operatively joined to the waste containment structure. Methods are provided for making the waste containment article.

9 Claims, 4 Drawing Sheets

U.S. PATENT DOCUMENTS

| | | | |
|---|---|---|---|
| 4,838,885 A | 6/1989 | Bernardin | 604/385.1 |
| 4,900,317 A * | 2/1990 | Buell | 604/385.2 |
| 4,938,753 A | 7/1990 | Van Gompel et al. | 604/385.2 |
| 4,938,754 A | 7/1990 | Mesek | 604/385.2 |
| 4,938,757 A | 7/1990 | Van Gompel et al. | 604/396 |
| 4,940,464 A | 7/1990 | Van Gompel et al. | 604/396 |
| 5,037,409 A | 8/1991 | Chen et al. | 604/358 |
| 5,098,423 A | 3/1992 | Pieniak et al. | 604/385.1 |
| 5,114,781 A | 5/1992 | Morman | 428/198 |
| 5,116,662 A | 5/1992 | Morman | 428/198 |
| 5,246,432 A * | 9/1993 | Suzuki et al. | 604/378 |
| 5,292,316 A * | 3/1994 | Suzuki | 604/385.2 |
| 5,387,210 A * | 2/1995 | Murakami | 604/385.01 |
| 5,391,162 A * | 2/1995 | Widlund et al. | 604/387 |
| 5,447,507 A * | 9/1995 | Yamamoto | 604/386 |
| 5,490,847 A * | 2/1996 | Correa et al. | 604/387 |

* cited by examiner

DISPOSABLE WASTE CONTAINMENT GARMENT

BACKGROUND OF THE INVENTION

This invention pertains to disposable waste containment articles, and more particularly to articles providing containment and absorbency of waste matter while being useful as a swimsuit garment.

Currently, disposable waste containment articles find widespread use in the areas of adult care, infant care, and child care, and have generally replaced reusable cloth articles. Disposable diapers, for example, have met a particular need and have become very popular. Disposable training pants have also met a particular need and have become popular. However, once a child desires to travel to a swimming pool or beach, the child requires a waste containment garment for possible "accidents" during such travel.

Although it is desired by the parent that the child not have an accident while wearing a swimsuit garment, accidents will occur and, during those times containment and limited absorbency is required. In addition, through the use of increased amounts of superabsorbents in disposable diapers and training pants, greatly enhanced absorbent capacities and leakage performance have been achieved under normal usage conditions. However, when infants and toddlers swim, the superabsorbent material (SAM) causes the diaper/pant to absorb water to its maximum capacity, therefore swelling to proportions typically not seen in normal use. The diaper/pant sags, becomes uncomfortable and heavy and does not fit under children's swimsuits. In some cases, the diaper/pant actually bursts, leaving globules of superabsorbent to litter the poolside or beach, or become clogged in pool filters. This also releases fecal matter contained in the diaper/pant. It is not uncommon for public pools to ban superabsorbent-containing diapers. However, the urine containment needs of children before they enter the water and the BM containment required in the water suggest that a containment garment is needed.

SUMMARY OF THE INVENTION

Thus, there is a need to provide an improved child's swimming apparel that minimizes the leakage of urine and fecal matter during travel to swimming while maintaining fecal containment during swimming. In response to this need, a new waste containment garment and method of making a waste containment garment have been discovered that contains a diaper-like waste containment structure to absorb urine when dry and contain BM when dry or wet. A waste containment garment according to the invention includes a waste containment structure having a longitudinal axis and opposite longitudinally spaced ends. The waste containment structure comprises an absorbent core, a backsheet and containment flaps. The structure contains little or no SAM so it does not swell up when wet. The absorbent is a mix of pulp and polymer coformed to give it durability when wet. The polymer-based fabric of the outer garment is lightweight, allowing for quick drying out of the water.

In another embodiment of the present invention there is provided a disposable waste containment article having a waste containment structure including a backsheet and an absorbent core, the backsheet having a pair of leg elastics along the longitudinal edges of the backsheet. A pair of containment flaps are joined to the waste containment structure outside the leg elastics.

In still another embodiment of the present invention there is provided a method of making a disposable waste containment article comprising the steps of providing a waste containment structure, supplying a pair of containment flaps having distal edges, placing the containment flaps with the waste containment structure and joining the containment flaps to the waste containment structure.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

BRIEF DESCRIPTION OF THE DRAWINGS

The above-mentioned and other features of the present invention and the manner of attaining them will become more apparent, and the invention itself will be better understood by reference to the following description of the invention, taken in conjunction with the accompanying drawings, wherein.

DEFINITIONS

Within the context of this specification, each term or phrase below will include the following meaning or meanings:

(a) "Bonded" refers to the joining, adhering, connecting, attaching, or the like, of two elements. Two elements will be considered to be bonded together when they are bonded directly to one another or indirectly to one another, such as when each is directly bonded to intermediate elements.

(b) "Disposable" includes being disposed of after use, and not intended to be washed and reused.

(c) "Disposed", "disposed on", "disposed with", "disposed at", "disposed near", and variations thereof are intended to mean that one element can be integral or unitary with another element, or that one element can be a separate structure joined to or connected to or placed with or placed near another element.

(d) "Elasticity" and "elastic" include that property of a material by virtue of which it tends to substantially recover to its original size and shape after removal of a force causing deformation of the material.

(e) "Elastically connected" and "elastically connecting" refer to two elements being separated by and bonded to an elastic member, where the relative position of the two elements may change due to extension of the elastic member.

(f) "Elongation" includes the ratio of the extension of a material to the length of a material prior to the extension. Elongation is expressed in percent.

(g) "Extension", "extend", and "extended" include the change in length of a material due to stretching. Extension is expressed in units of length.

(h) "Force" includes a physical influence exerted by one body on another which produces acceleration of bodies that are free to move and deformation of bodies that are not free to move. Force is expressed in grams-force.

(i) "Foreshortened" and "foreshortening" include to shorten beforehand, that is, before a subsequent step.

(j) "Front" and "back" are used to designate relationships relative to the garment itself, rather than to suggest any position the garment assumes when it is positioned on a wearer.

(k) "Member" when used in the singular can have the dual meaning of a single element or a plurality of elements.

(l) "Operatively joined" with reference to the attachment of an elastic member to another element means that the elastic member when attached to or connected to or treated with heat with the element gives that element elastic properties. With reference to the attachment of a non-elastic member to another element, it means that the member and element can be attached in any suitable manner that permits or allows them to perform the intended or described function of the joinder. The joining, attaching, connecting or the like can be either directly, such as joining either member directly to an element, or can be indirectly by means of another member or element disposed between the first member and the first element.

(m) "Pervious" means that a layer of material is able to pass or transport a detectable amount of liquid under conditions normally encountered in a diaper/pant during use.

(n) "Porous" means that a layer of material is able to pass or transport a measurable amount of liquid under conditions normally encountered in a diaper/pant during use.

(o) "Rupture" includes the breaking or tearing apart of a material; in tensile testing, rupture refers to the total separation of a material into two parts either all at once or in stages, or the development of a hole in some materials.

(p) "Stretch bonded" refers to an elastomeric strand being bonded to another member while the elastomeric strand is elongated at least about 25 percent of its relaxed length. Desirably, the term "stretch bonded" refers to the situation wherein the elastomeric strand is elongated at least about 100 percent, more desirably at least about 300 percent, of its relaxed length when it is bonded to the other member.

(q) "Stretch bonded laminate" ("SBL") refers to a composite material having at least two layers in which one layer is a gatherable layer and the other layer is a stretchable, that is, elastic, layer. The layers are joined together when the stretchable layer is in a stretched condition so that upon relaxing the layers, the gatherable layer is gathered.

(r) "Tension" includes a uniaxial force tending to cause the extension of a body or the balancing force within that body resisting the extension.

(s) "Two-dimensional" refers to a garment, such as a diaper, that can be opened and laid in a flat condition without destructively tearing any structure. This type of garment does not have continuous leg and waist openings when opened and laid flat, and requires a fastening device, such as adhesive tapes, to attach the garment about the wearer.

(t) "Three-dimensional" refers to a finished garment similar to shorts or pants in that they have continuous leg and waist openings that are bounded by the material of which the garment is made. This type of garment can be opened and laid flat only by destructively tearing it. This type of garment may or may not have manually tearable seams.

(u) "Ultimate elongation" includes the elongation at the point of rupture.

These definitions are not intended to be limiting and these terms may be defined with additional language in the remaining portion of the specification.

DESCRIPTION OF A PREFERRED EMBODIMENT

Figure 1:
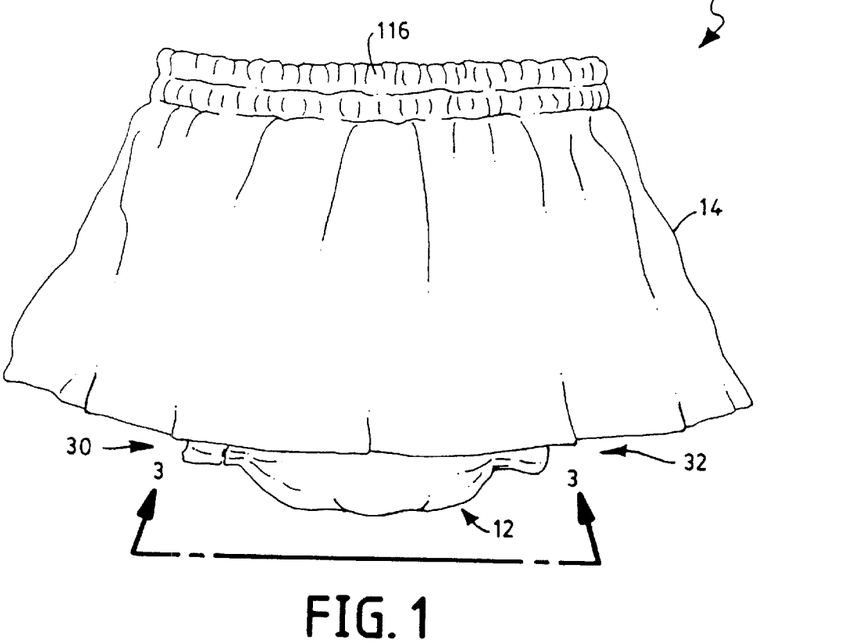
FIG. 1 is a front view of a pant typifying an embodiment of the present invention for a girl's swimsuit.
Figure 2:
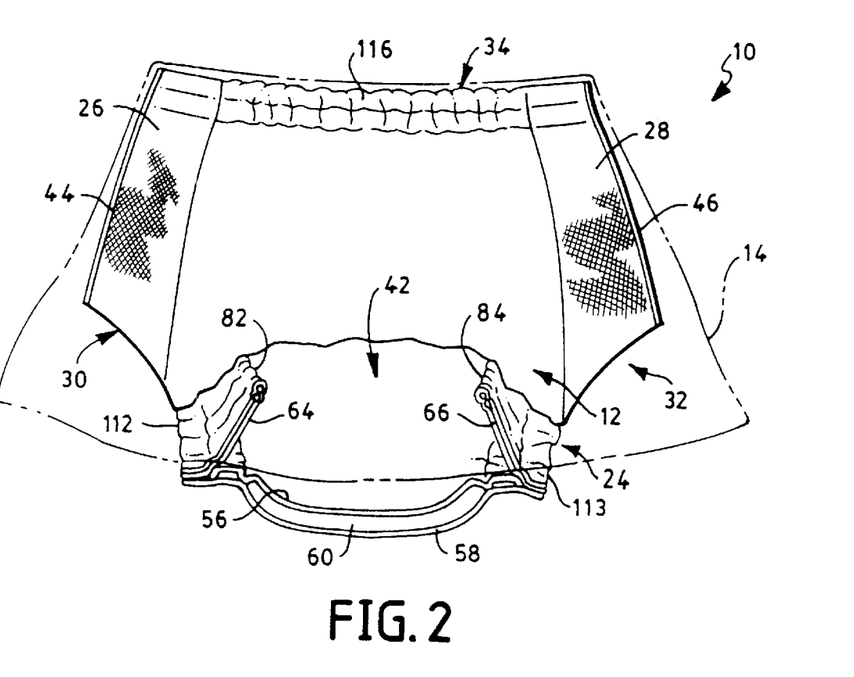
FIG. 2 is a front view of a pant typifying an embodiment of the present invention for a girl's swimsuit.

A pant 10 using this invention, shown in FIGS. 1 and 2, includes a waste containment structure 12, which can be made or constructed in a variety of ways, one of which is described in U.S. patent application Ser. No. 043,132 filed on Mar. 25, 1993, which is incorporated by reference herein. Other pant designs are described in U.S. Pat. Nos. 4,938,757, 4,747,846, and 4,940,464; the contents of these three patents are incorporated by reference herein.

Figure 7:
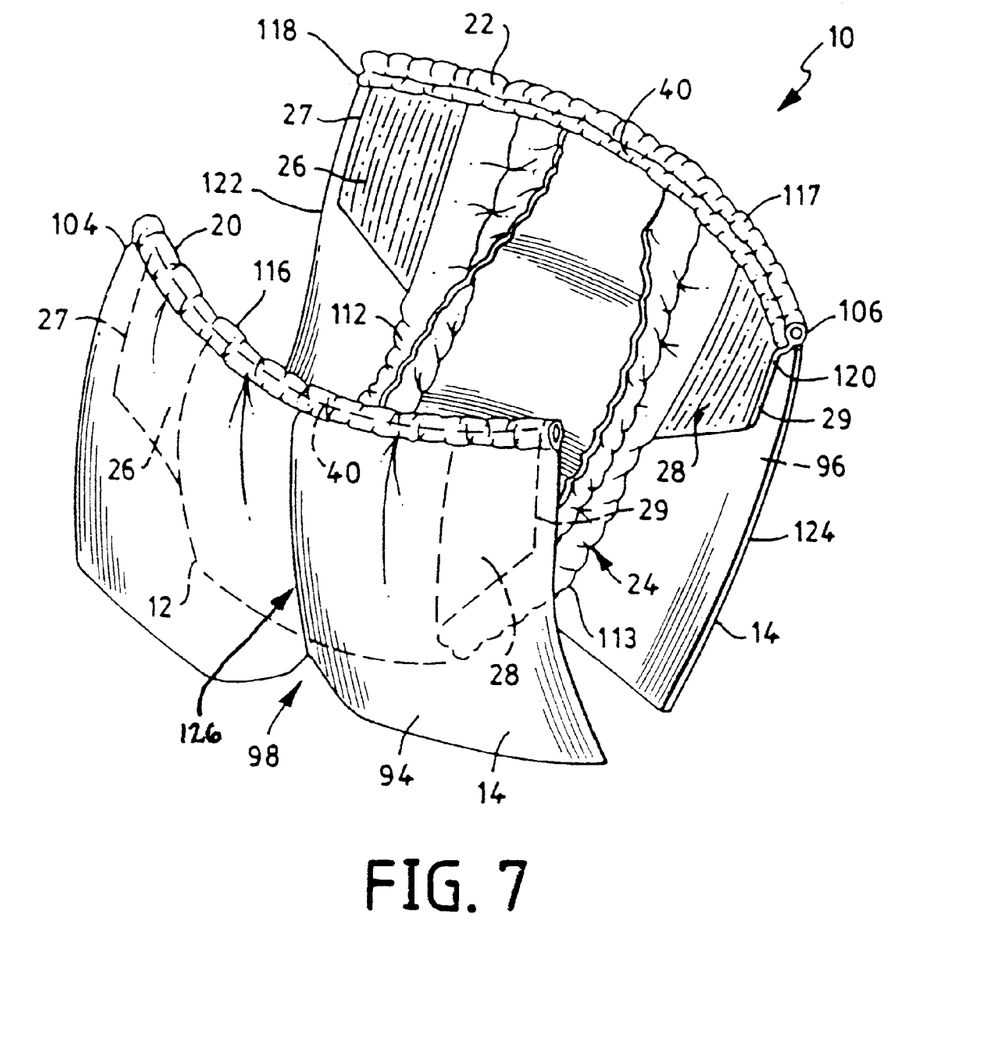
FIG. 7 is a perspective view of a pant for a boy's swimsuit showing the invention in an opened out view.

The pant 10 is illustrated partially opened out in FIG. 7. The structure 12 includes front and back longitudinally spaced waist regions 20 and 22, which terminate in longitudinal ends of the pant 10. A crotch area 24 is located between the front and back waist regions 20 and 22. The waist regions 20 and 22 together with crotch area 24 form a waste containment section 42 (FIG. 2). Left and right side panels 26 and 28 extend between the front and back waist regions 20 and 22.

As illustrated most clearly in FIGS. 2 and 7, the edges 27 and 29 of side panels 26 and 28 may be bonded together in the finished pant to form manually tearable, non-refastenable seams 44 and 46. The seams 44 and 46 may be formed by any suitable means such as ultrasonic sealing, adhesive bonding, heat sealing, or the like. One suitable method of forming such seams is disclosed in U.S. Pat. No. 4,938,753 issued Jul. 3, 1990, to Van Gompel et al., which is incorporated herein by reference. The waste containment structure 12 thus defines a waist opening 34 and a pair of leg openings 30 and 32 (FIGS. 1 and 2).

In FIG. 2, waste containment structure 12 generally comprises waste containment section 42 and side panels 26 and 28. Side panels 26 and 28, which may or may not have elastic characteristics, are ultrasonically bonded and are formed such that the materials of construction provide a manually tearable, nonrefastenable region near the seams 44 and 46. The side panels 26 and 28 can be rendered elastic by incorporating a layer of elastic material or an SBL. Alternatively, the structure 12 can be rendered elastic by incorporating strands of elastics about the body of the structure or by incorporating a layer of elastic material or an SBL throughout the exterior of the structure 12.

Figure 3:
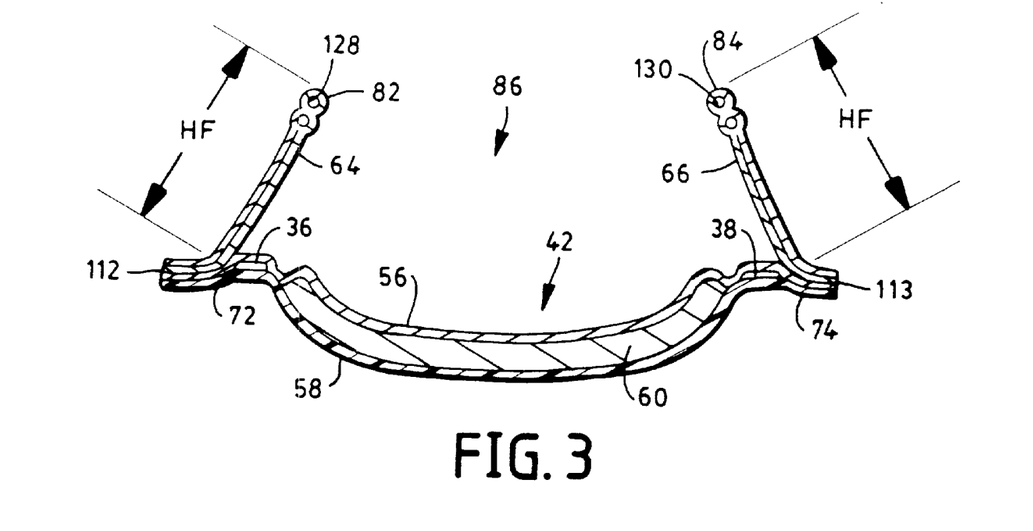
FIG. 3 is a cross-sectional view of FIG. 1 taken along line 3—3 and viewed in the direction of the arrows.

Waste containment section 42 includes the containment flaps 64 and 66, backsheet 58, liner 56, absorbent core 60 and side panels 26 and 28. Containment flaps 64 and 66 have respective distal ends 82 and 84. FIG. 3 shows the generally upright position containment flaps 64 and 66 assume when pant 10 is being pulled on and worn. It is understood that, although waste containment structure 12 is illustrated here as being flat for ease of understanding, waste containment structure 12, in fact, assumes a bowed or bucket-like shape in the crotch area 24 as illustrated in FIGS. 2 and 3.

One specific method of attachment is described in U.S. patent application Ser. No. 054,508 filed Apr. 26, 1993 and assigned to the assignee of this application; the contents of this patent application is incorporated by reference herein. The proximal edges of flaps 64 and 66 may be attached inboard or outboard of the leg elastics 36 (FIG. 3) and 38, however, it is desirable that they be placed outboard.

With reference to FIGS. 3 and 7, the waste containment structure 12 as illustrated includes a backsheet 58, a substantially liquid permeable bodyside liner 56, and an absorbent core 60 sandwiched between the backsheet and the liner. The backsheet 58 and bodyside liner 56 are desirably longer and wider than the absorbent core 60, so that the peripheries of the backsheet and liner form margins which may be sealed together using ultrasonic bonds, thermal bonds, adhesives, or other suitable means. The absorbent core 60 may be attached to the backsheet 58 and/or the bodyside liner 56 using ultrasonic bonds, adhesives, or other suitable means. The waste containment structure 12 may also include additional components to assist in the acquisition, distribution and storage of waste material. For example, the waste containment structure 12 may include a transport layer, such as described in U.S. Pat. No. 4,798,603 issued Jan. 17, 1989, to Meyer et al., or a surge management layer, such as described in European Patent Application EP 0 539 703 A1, published May 5, 1993, which patent and application are incorporated herein by reference.

Leg elastics 36 and 38 can be stretch bonded to the cover material along the longitudinal edges of the structure 12. The waist elastic 116 and 117 elasticize the waist regions 20 and 22 of the waste containment structure 12. Thereafter, each side panel 26 and 28 can be bonded together by seams 44 and 46 (FIG. 2) so that the waste containment structure 12 defines the waist opening 34 and the pair of leg openings 30 and 32. The two leg elastics are placed desirably from about 10 to about 16 cm apart for a 17 to 30 pound child.

Figure 5:
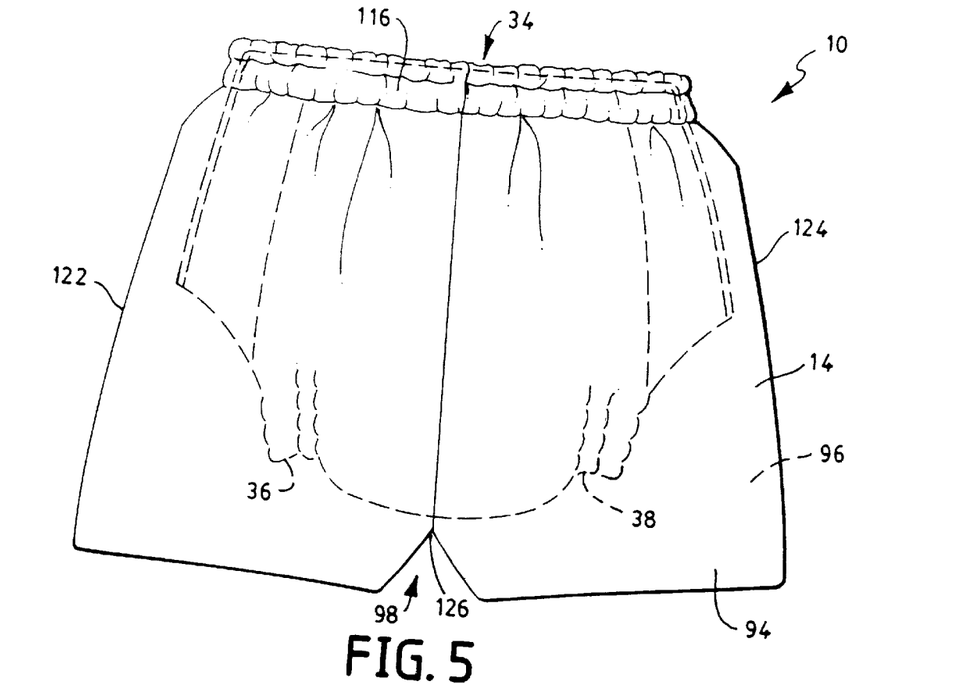
FIG. 5 is a front view of a pant for a boy's swimsuit showing the crotch area of the cover.

In FIG. 7, pant 10 is in a partial opened state showing edges 27 and 29 which are joined to form seams not shown, thus forming the finished training pant 10. In FIGS. 5 and 7, to construct the cover 14 of the preferred embodiment for training pant 10, the front panel section 94 may be joined with the back panel 96 along seams 122 and 124 and in the case of a boxer short at crotch area seam 126 and to waste containment structure 12 at front and back waist regions 20 and 22 near the waist opening 34. The term "finished pant" means a three-dimensional training pant that can be used for its intended purpose. The waste containment structure 12 may optionally be T-shaped, I-shaped, hourglass-shaped, or irregularly-shaped.

In FIG. 3, the waste containment structure 12 also desirably includes leg elastics 36 and 38 operatively joined to the backsheet 58, the bodyside liner 56, or both. The leg elastics 36 and 38 are positioned along the edges of side panels 26 and 28 and the longitudinal edges 112 and 113 of the waste containment structure 12 in the crotch area 24. The leg elastics 36 and 38 may assist in holding the waste containment structure 12 against the body of the wearer or forming seals or gaskets about the legs of the wearer.

The waste containment structure 12 can be constructed by supplying bodyside liner and backsheet materials and sandwiching an individual absorbent core 60 between the backsheet 58 and bodyside liner 56. The side peripheries of the backsheet 58 and bodyside liner 56 outward of the absorbent core 60 can be joined with side panel material. Individual waste containment structure 12 can then be cut from the continuous supply of backsheet and bodyside liner materials.

Figure 4:
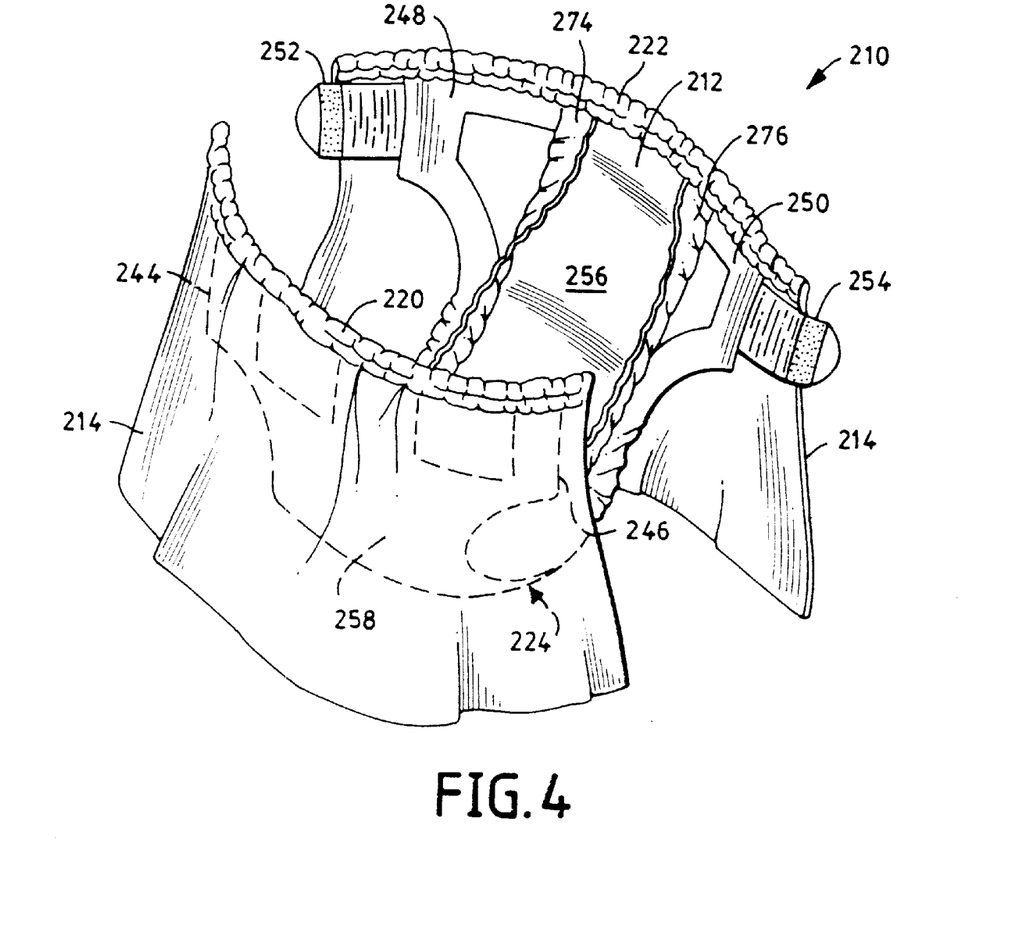
FIG. 4 is a perspective view of a diaper embodying the present invention and showing the opening/closing arrangement.
Figure 6:
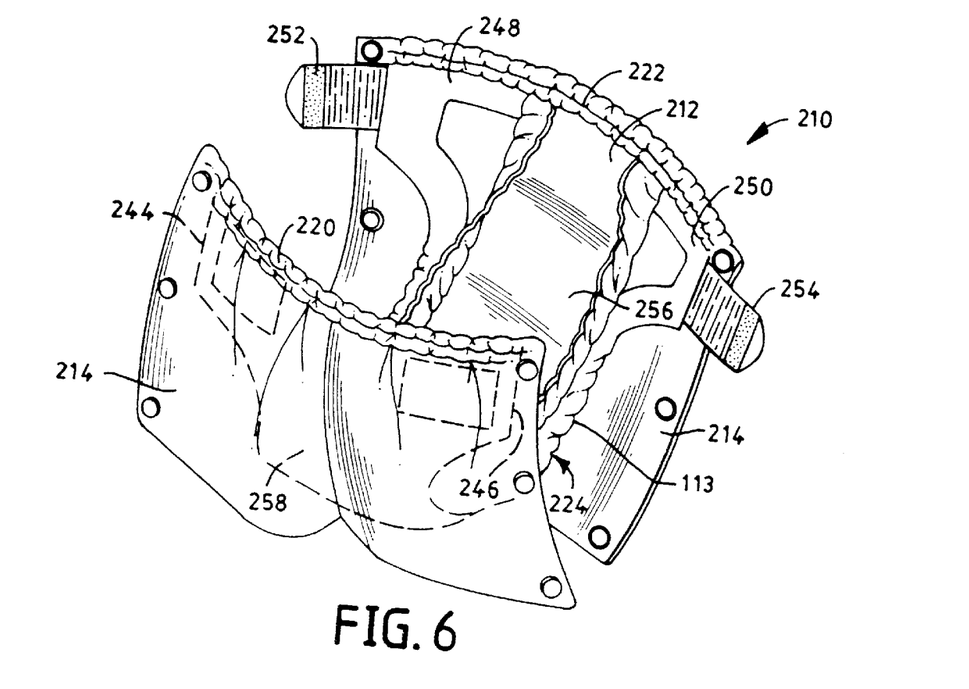
FIG. 6 is a perspective view diaper for a boy's swimsuit view showing embodying the present invention and showing the opening/closing arrangement.

Referring primarily to FIGS. 4 and 6, a disposable, two-dimensional garment is shown as diaper 210. The diaper 210 includes waste containment structure 212, front waist region 220 including oppositely disposed front ear sections 244 and 246, back waist region 222 including fasteners 252 and 254 on respective oppositely disposed back ear sections 248 and 250, and crotch area 224 between front waist region 220 and back waist region 222. Diaper 210 may further comprise a cover 214.

The waste containment structure 212 further comprises a backsheet 258, a liner 256, and an absorbent core (not shown) disposed between backsheet 258 and liner 256. Waste containment structure 12 includes containment flaps 274 and 276 having elastic members (not shown) attached thereto.

A more detailed description of the structure of a typical diaper 210, its process of manufacture, and method of use are contained in U.S. Pat. No. 4,704,116, which is assigned to the assignee of the present invention, the contents of which are incorporated by reference herein.

For application of the diaper to an infant and in reference to FIG. 4, the infant may be placed upon back waist region 222 of diaper 210 in preparation of fitting and attaching the diaper 210. The legs of the infant are spread apart so that front waist region 220 can be easily folded upwardly over the front of infant in a manner that snugly fits crotch area 224 against the infant. Thereafter, fasteners 252 and 254 are attached to the outermost surface of respective front ear sections 244 and 246.

The absorbent core 60 is desirably relatively thin to provide an overall thinness dimension to the pant 10. The absorbent core 60 desirably has a bulk thickness which is not more than about 1.25 cm, and particularly not more than about 0.7 cm when dry. The thickness is measured according to the thickness test shown in the Example. The bulk thickness is determined under a restraining pressure of 0.2 pounds per square inch (1.38 kPa). Further, the absorbent core 60 suitably has an absorbent capacity of at least about 60 grams, and desirably at least about 100 grams, of synthetic urine. The capacity is measured according to the saturation capacity that is shown in the Example.

The coform material may comprise an airlaid blend of cellulosic wood fibers and meltblown polyolefin fibers, such as polyethylene or polypropylene fibers, or may comprise an air-formed batt of cellulosic fibers (i.e., wood pulp fluff). Optionally, the absorbent core 60 may be treated with a surfactant to aid in liquid acquisition when in a dry environment. In particular embodiments of the invention, the absorbent core 60 has a bulk thickness of not more than about 1.25 cm when dry. The hydrophilic fibers and polymer strands may be provided in a fiber-to-polymer ratio which is less than 80:20, for example between about 30:70 and about 80:20 and, desirably between about 60:40 and about 70:30.

The absorbent core 60 can comprise a coform material composed of a mixture of cellulosic fibers and synthetic polymer fibers. For example, the coform material may comprise an airlaid blend of cellulosic wood fibers and meltblown polyolefin fibers, such as polyethylene or polypropylene fibers. Absorbent core 60 can comprise only coform, or a combination of superabsorbent materials and coform, with other absorbent or non-absorbent materials. Optionally, the core may be treated with a surfactant to aid in liquid acquisition when in a dry environment. In particular embodiments of the invention, the absorbent core has a bulk thickness of not more than 0.9 cm when wet. Preferably, the wet bulk thickness is less than 0.8 cm. The core should be flexible across the diaper so as to encourage formation of a bucket in the crotch region of the structure 12.

For absorbent core 60, compounds to increase the core absorbency, are included in an effective amount and may consist of organic or inorganic high-absorbency materials. For example, the absorbent core 60 can include 0–5 weight percent high-absorbency material, preferably less than 1%. Suitable inorganic high-absorbency materials include, for example, absorbent clays and silica gels.

Organic high-absorbency materials can include natural materials, such as pectin, guar gum and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyrridine or the like. Other suitable polymers can include hydrolyzed acrylonitrile grafted starch, acrylic acid grafted starch, and isobutylene maleic anhydride copolymers, and mixtures thereof.

The hydrogel polymers are preferably sufficiently cross-linked to render the materials substantially water-insoluble. Cross-linking may, for example, be by irradiation or by covalent, ionic, van der Waals or hydrogen bonding. Suitable materials are available from various commercial vendors, such as Dow Chemical Company, Hoechst-Celanese Corporation and Allied-Colloid. Typically, the high-absorbency material is capable of absorbing at least about 15 times its weight in water, and preferably is capable of absorbing more than about 25 times its weight in water.

The high-absorbency material can be distributed or otherwise incorporated into the absorbent core 60 employing various techniques. For example, the high-absorbency material can be substantially uniformly distributed among the fibers comprising the absorbent core. The materials can also be nonuniformly distributed within the absorbent core fibers to form a generally continuous gradient with either an increasing or decreasing concentration of high-absorbency material, as determined by observing the concentration moving inward from the backsheet 58. Alternatively, the high-absorbency material can comprise a discrete layer separate from the fibrous material of the absorbent core 60, or can comprise a discrete layer integral with the absorbent core.

The absorbent core 60 may also include a wrap layer to help maintain the integrity of the fibrous core. This wrap may comprise a hydrophilic spunbond, meltblown or bonded-carded web material composed of synthetic polymer filaments, such as polypropylene, polyethylene, polyesters or the like or natural polymer filaments such as rayon or cotton.

The bodyside liner 56 may be any soft, flexible, porous sheet which passes fluids therethrough. Again, the liner must permit submersion in fresh water, salt water, or treated water and still retain its integrity. The bodyside liner 56 may comprise, for example, a nonwoven web or sheet of a spunbonded, meltblown or bonded-carded web composed of synthetic polymer filaments, such as polypropylene, polyethylene, polyesters or the like, or a web of natural polymer filaments such as rayon or cotton. The bodyside liner 56 has a pore size that readily allows the passage therethrough of liquids, such as urine and other body exudates. The liner 56 may be selectively embossed or perforated with discrete slits or holes extending therethrough. Optionally, the web or sheet may be treated with a surfactant to aid in liquid transfer. One suitable bodyside liner material is a wettable spunbonded polypropylene web produced by the methods and apparatus described in U.S. Pat. No. 4,340,563 issued Jul. 20, 1982, and U.S. Pat. No. 4,405,297 issued Sep. 23, 1983, to Appel et al., which are incorporated herein by reference. Bodyside liner 56 is liquid permeable and is a spunbonded polypropylene nonwoven web having a basis weight of about 0.75 oz/yd$^2$ (25.4 gsm). Suitable adhesives for adhering the laminate layers can be obtained from Findley Adhesives, Inc. of Wauwatosa, Wis.

The backsheet 58 may comprise a thin, liquid impermeable web or sheet of plastic film such as polyethylene, polypropylene, polyvinyl chloride or similar material. Alternately, the backsheet 58 may comprise a nonwoven, fibrous web which has been suitably constructed and arranged to have low liquid perviousness. Still alternately, the backsheet may comprise a layered or laminated material, such as a thermally bonded plastic film and nonwoven web composite. Since the garment is typically intended for active wear, an exposed backsheet or portions thereof, can be made of materials or of a basis weight which is abrasion resistent.

The backsheet 58 may be constructed of a single spunbonded polypropylene nonwoven web having a basis weight of about 0.5 oz/yd$^2$ (17 gsm) to about 2.0 oz/yd$^2$ (68 gsm). In the case of a boy's boxer short type article, the cover preferably comprises a material having a basis weight of from about 0.5 oz/yd$^2$ (23.8 gsm) to about 2.0 oz/yd$^2$ (68 gsm). In the case of a girl's skirt type article, the cover preferably comprises a material having a basis weight of from about 0.5 oz/yd$^2$ (23.8 gsm) to about 2.0 oz/yd$^2$ (68 gsm), preferably 1.0 oz./yd$^2$ to 2.0 oz./yd$^2$ at least in the crotch and buttocks regions of the backsheet. Lesser basis weights may be used in other regions of the article.

The elastic side panel material desirably has stretch characteristics in a first direction such that it is capable of from about 10 to about 500 percent elongation and upon release of tension will recover at least 55 percent of its elongation. It is generally preferred that the side panel material in the first direction be capable of between about 50 and about 300 percent elongation, particularly at least 125 percent elongation and recovery upon release of tension of at least 80 percent of its elongation.

As described previously, the side panels 26 and 28 may be formed of a material capable of stretching in one direction or capable of stretching in at least two substantially perpendicular directions. One suitable one-directional stretch material is disclosed in U.S. Pat. No. 4,720,415 issued Jan. 19, 1988, to Vander Wielen et al., which is incorporated herein by reference. The one-directional stretch material may comprise a composite material including at least one gatherable web bonded to at least one elongated elastic web. The elastic web may be an elastic film or nonwoven fibrous elastic webs such as meltblown elastomeric fibrous webs. In one embodiment, the side panels comprise a stretch bonded laminate formed of a prestretched elastic meltblown inner layer sandwiched between and attached to a pair of spunbond polypropylene nonwoven webs having a basis weight of about 0.4 oz/yd$^2$ (13.6 gsm). Suitable elastic materials can be purchased from the Shell Chemical Company of Houston, Texas under the trade name Kraton. Other suitable one-directional stretch materials are disclosed in U.S. Pat. No. 4,606,964 issued Aug. 19, 1986, to Wideman and U.S. Pat. No. 4,657,802 issued Apr. 14, 1987, to Morman.

Suitable two-directional stretch materials for the side panels 26 and 28 are disclosed in U.S. Pat. No. 5,114,781 issued May 19, 1992, and U.S. Pat. No. 5,116,662 issued May 26, 1992, to Morman, which are incorporated herein by reference.

A two-directional stretch material may comprise a composite material including a neckable material and an elastic sheet, which may be formed by meltblowing or extrusion. Neckable materials are those which may be constricted in at least one dimension by applying a tensioning force in a direction perpendicular to the desired direction of neckdown, and may include a spunbonded, meltblown or bonded carded web. The tensioned, necked neckable material may be joined to the elongated elastic sheet at spaced locations arranged in a nonlinear configuration. Another two-directional stretch composite material may comprise one or more layers of reversibly necked material joined to one or more layers of elastic sheet at spaced locations. Reversibly necked materials are those that have been treated, such as with heat, while necked to impart memory to the material so that, when a force is applied to extend the material to its pre-necked dimensions, the treated, necked portions will generally recover to their necked dimensions upon termination of the force.

In reference to FIG. 3, each containment flap 64 and 66 has a flap height, HF, measured between the respective distal edges 82 and 84 and respective proximal edges 72 and 74 (see FIG. 3). Flap height HF has a range between about 2 cm to about 8 cm, and a desired range of about 3 cm to about 5 cm.

Flap height HF and the elastic characteristics of flap elastics 128 and 130 determine the anatomical location of distal edges 82 and 84 and well 86 at the crotch of the wearer. For example, distal edges 82 and 84 can shift too close together such that flaps 64 and 66 form a tent over absorbent core 60, thereby preventing absorption of urine or other waste matter.

The containment flap material may comprise a thin, liquid impermeable web or sheet of plastic film such as polyethylene, polypropylene, polyvinyl chloride or similar material. Alternately, the flap material may comprise a nonwoven, fibrous web which has been suitably constructed and arranged to have low liquid perviousness. Still alternately, the flaps may comprise a layered or laminated material, such as a thermally bonded plastic film and non-woven web composite. The flap material, films or nonwoven, may be apertured to increase the porous nature of the flap. Desirably, such apertures have a density of 10/cm$^2$ and have a diameter of about 0.125 cm.

It is desirable to provide consistent containment flap positioning within the crotch of the wearer as shown in FIGS. 3 and 4. Additionally, because of the relatively large dimension of flap height HF, when absorbent core 60 becomes heavier due to the absorption of waste matter and begins to sag downwardly, containment flaps 64 and 66 will extend to maintain their seal, thereby containing liquid and other waste matter in volume well 86 until absorbent core 60 has time to absorb the liquid waste matter in a dry environment, and the liquid has had time to strain through the flap to leave the solid waste matter in the volume well 86 in a wet environment or upon exit from a wet environment. Preferably, the liquid initially trapped when a wearer first leaves a swimming pool will drain from the waste containment structure rather quickly, desirably in less than 30 seconds.

In reference to FIG. 3, flap elastics 128 and 130, which may be a single ribbon of elastic material or a plurality of strands of elastic material, have a predetermined elongation and tension in order to assist in properly positioning containment flaps 64 and 66. In order for containment flaps 64 and 66 to assume a desired upright orientation, as shown in FIG. 3, to contact and seal against wearer's thighs, each flap elastic 128 and 130 desirably has a minimum of about 90 percent elongation when incorporated into flap 64 and 66 of a finished pant 10. A desired range of elongation is between about 90 percent to about 150 percent stretch. A desired tension range for each flap elastic 128 and 130 is between about 90 grams-force to about 200 grams-force at 90 percent of ultimate elongation.

Flap elastics 128 and 130 in containment flaps 64 and 66 are strands of Lycra T151 940 decitex elastic which can be obtained from E. I. du Pont de Nemours Co., Wilmington, Del. The flap material is a spunbond polypropylene nonwoven web having a basis weight of about 0.7 oz/yd$^2$ (23.7 gsm). It is desired that the nonwoven layer be at least liquid permeable and preferably liquid porous.

As absorbent core 60 becomes heavier due to its absorbing waste, absorbent core 60 will tend to sag or move downwardly, away from the crotch. However, containment flaps 64 and 66 will be able to extend in height, as shown in FIG. 3, to maintain the seal against the crotch. Although the absorbent core 60 will have a tendency to sag, it will also expand, thereby filling a portion of well 86. In this invention, the absorbency is desirably limited to provide a wet diaper BM containment of at least about 250 cm$^3$ in the wet state, desirably 300 cm$^3$ and more desirably 400 cm$^3$. For purpose of this invention wet state is treated garment with water in an amount equal to its saturation capacity as described in the Example. The garment for test purposes should have a width between the proximal edges of the containment flaps not greater than 14 cm and a length of the overall garment of not greater than 43 cm.

The leg elastics 36 and 38 may be formed of a stretch bonded laminate. In particular, the stretch bonded laminate may comprise at least one nonwoven gatherable layer and an elastic layer. Alternately, the leg elastics 36 and 38 may be formed of a dry-spun coalesced multifilament elastomeric thread sold under the tradename LYCRA and available from I.E. Du Pont de Nemours and Company. Still alternately, the elastics may be formed of other typical elastics utilized in the diaper-making art, such as a thin ribbon of elastic material as disclosed in U.S. Pat. No. 4,940,464 issued Jul. 10, 1990, to Van Gompel et al., which is incorporated herein by reference. Elasticity could also be imparted to the longitudinal side sections by extruding a hot melt elastomeric adhesive between the backsheet 58 and the bodyside liner 56. Other suitable elastic gathering means are disclosed in U.S. Pat. No. 4,938,754 to Mesek and U.S. Pat. No. 4,388,075 to Mesek et al.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, only one rather than both ends of the waste containment structure can be elastically connected to the cover. Therefore, the invention should not be limited by the specific embodiments described, but only by the claims. The materials of which pant 10 are made, including containment flaps 64 and 66 can be any materials specifically desired by the user or manufacturer. Numerous examples of materials used in constructing pant 10 and diaper 210 are described in the aforementioned U.S. patents and patent applications incorporated by reference herein.

EXAMPLE

Bulk Thickness Wet and Dry and the Saturated Capacity

Each product was opened, the leg elastics snipped and laid flat. The product was sectioned into three parts, front, center and back. Using an AMES thickness gauge under 0.2 psi pressure, the thickness was measured for each section, the front, center and back, and recorded as shown in Table I below. The weight of each section while dry was measured using Mettler scale and recorded. The sections were then submerged in a bath of tap water for ½ hour. The sections were removed from the bath and placed on open screen for 5 minutes to allow excess water to drip out of each section. Each section was then weighed and the saturated weight results were recorded as shown in Table II below. Each section was then measured under the AMES thickness gauge using 0.2 psi and the saturated thickness was recorded as shown in Table I below.

A Product of this invention
B HUGGIES® Supertrim Step 3 diaper manufactured by Kimberly-Clark Corporation, Neenah, Wis.
C PAMPERS® Ultra Dry Thin Crawler/Walker diaper manufactured by Procter & Gamble Company
D HUGGIES® PULL-UPS® training pant manufactured by Kimberly-Clark Corporation
E DRYPERS® diaper manufactured by Drypers Corporation
F FITTI® diaper manufactured by Associated Hygienics Corporation
G WONDER DRYS® diaper manufactured by Paragon Trade Brands Corporation

TABLE I

THICKNESS, mm

| | | Back | Middle | Front | Average | Standard Deviation |
|---|---|---|---|---|---|---|
| A | Dry | 4.08 | 8.14 | 5.36 | 5.86 | 2.08 |
|   | Wet | 4.72 | 8.16 | 5.60 | 6.16 | 1.79 |
| B | Dry | 3.58 | 6.36 | 5.13 | 5.02 | 1.39 |
|   | Wet | 28.70 | 33.68 | 33.80 | 32.06 | 2.91 |
| C | Dry | 5.26 | 8.68 | 5.60 | 6.51 | 1.88 |
|   | Wet | 33.90 | 34.72 | 34.15 | 34.26 | .42 |
| D | Dry | 9.83 | 11.52 | 13.43 | 11.59 | 1.80 |
|   | Wet | 31.70 | 34.79 | 34.77 | 33.75 | 1.78 |
| E | Dry | 9.03 | 10.32 | 8.90 | 9.42 | .79 |
|   | Wet | 11.56 | 12.20 | 13.08 | 12.28 | .76 |
| F | Dry | 9.45 | 10.20 | 8.42 | 9.36 | .89 |
|   | Wet | 25.86 | 20.85 | 17.31 | 21.34 | 4.30 |
| G | Dry | 6.24 | 8.36 | 6.37 | 6.99 | 1.19 |
|   | Wet | 25.80 | 24.70 | 32.10 | 27.53 | 3.99 |
| H | Dry | 3.35 | 6.38 | 4.83 | 4.85 | 1.52 |
|   | Wet | 4.74 | 9.89 | 8.36 | 7.66 | 2.64 |

TABLE II

Saturation Capacity, g

| A | 160.66 |
|---|---|
| B | 1274.11 |
| C | 1403.75 |
| D | 976.01 |
| E | 553.59 |
| F | 913.84 |
| G | 1175.55 |
| H | 277.83 |

To determine the wet solid waste capacity:

Each product was treated with tap water in an amount equal to its respective saturation capacity. The product was allowed to equilibrate for 2 minutes. The wet product was then placed in a normal position on a standing baby model. A flexible PVC plastic tube having a diameter of 3/16 inch was positioned between the product and the baby model at a location which approximated that of the anus of a baby. Synthetic BM was prepared using the following ingredients: 300 grams of Betty Crocker Potato Buds (manufactured by General Mills Co.) 75 grams Betty Crocker brownie mix (manufactured by General Mills Co.) and 1365 ml of tap water. Synthetic BM was then added to the back crotch area of each product through the plastic tube using a 60 cc syringe, having a 30 mm inside cylindrical diameter and an outlet tip diameter of 4 mm and attached to the tube. The synthetic BM was pumped into the product until leakage was visually detected at the leg openings of the product. A reading in cubic cm of total synthetic BM pumped in was taken at point of failure, i.e. just as synthetic BM began to leak out of product. The results are shown in Table III below.

TABLE III

BM Capacity, $cm^3$

| A | 425 |
|---|---|
| B | 165 |
| C | 143 |
| D | 180 |
| E | 120 |
| F | 68 |
| G | 160 |
| H | 80 |

While this invention has been described as having a preferred embodiment, it will be understood that it is capable of further modifications. This application is thereby intended to cover any variations, equivalents, uses, or adaptations of the invention following the general principles thereof, and including such departures from the present disclosure as come within known or customary practice in the art to which this invention pertains and fall within the limits of the appended claims.

What is claimed is:

1. A disposable waste containment article, comprising:
   a waste containment structure comprising a backsheet and an absorbent core on said backsheet, and
   a pair of liquid pervious containment flaps joined to said structure wherein the thickness when wet of said absorbent core is less than about 0.9 cm, wherein said containment flaps comprise an apertured material wherein said aperatures have a density of at least about 10 per square cm, said apertures having a diameter of at least 0.125 cm.

2. The article of claim 1 wherein the thickness of said absorbent core in the dry state is less than about 1.25 cm.

3. The article of claim 2 wherein the thickness of said absorbent core in the wet state is less than about 0.8 cm.

4. The article of claim 1 wherein the waste containment structure further comprises a volume well formed between said core and said flaps for holding solid body exudates.

5. The article of claim 4 wherein said volume well holds at least about 250 cm$^3$ of solid exudates in the wet state.

6. The article of claim 5 wherein said volume well holds at least about 300 cm$^3$ of solid exudates in the wet state.

7. The article of claim 6 wherein said volume well holds at least about 400 cm$^3$ of solid exudates in the wet state.

8. The article of claim 1 wherein the waste containment structure comprises a liner to which said flaps are operatively joined, said liner and flaps forming a volume well for holding solid exudates.

9. The article of claim 8 wherein the volume well holds at least about 250 cm$^3$ of solid waste in the wet state.

\* \* \* \* \*